(12) United States Patent
Tröllsch

(10) Patent No.: US 7,884,939 B2
(45) Date of Patent: Feb. 8, 2011

(54) GAS-MEASURING ARRANGEMENT WITH AN OPEN OPTICAL MEASURING SECTION

(75) Inventor: Arne Tröllsch, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 163 days.

(21) Appl. No.: 12/389,562

(22) Filed: Feb. 20, 2009

(65) Prior Publication Data
US 2009/0279094 A1 Nov. 12, 2009

(30) Foreign Application Priority Data
May 6, 2008 (DE) ............. 10 2008 022 222

(51) Int. Cl.
*G01N 21/59* (2006.01)
(52) U.S. Cl. ................... 356/437; 356/419
(58) Field of Classification Search ......... 356/432–440, 356/419; 250/339.13, 339.06
See application file for complete search history.

(56) References Cited

U.S. PATENT DOCUMENTS

| 4,746,218 A * | 5/1988 | Lord, III ............... 356/437 |
| 5,339,155 A | 8/1994 | Partridge et al. |
| 5,767,976 A | 6/1998 | Ankerhold et al. |
| 7,636,153 B2 * | 12/2009 | Willing et al. ............ 356/72 |
| 2008/0198381 A1 * | 8/2008 | Heggs et al. ............ 356/437 |

FOREIGN PATENT DOCUMENTS

| EP | 1286154 A1 | 2/2003 |
| JP | 58213237 A | 12/1983 |

* cited by examiner

*Primary Examiner*—Hoa Q Pham
(74) *Attorney, Agent, or Firm*—McGlew and Tuttle, P.C.

(57) ABSTRACT

A gas-measuring arrangement (1) with an open optical measuring section (7) is formed by a measuring device (5) with an array of lenses (10, 12, 19, 24), a phase mask (22), an optical path mirror (16) positioned obliquely, and a reflecting mirror (3) located outside the measuring device (5) at the end of the open measuring section (7). The light is decoupled to a detector (26) via a phase mask (22) and the optical path mirror (16). The phase mask (22) diverges a light intensity spot and the light intensity ring is decoupled by an obliquely positioned optical path mirror (16) towards a detector (26).

20 Claims, 4 Drawing Sheets

GAS-MEASURING ARRANGEMENT WITH AN OPEN OPTICAL MEASURING SECTION

CROSS REFERENCE TO RELATED APPLICATIONS

This application claims the benefit of priority under 35 U.S.C. §119 of German Patent Application DE 10 2008 022 222.4 filed May 6, 2008, the entire contents of which are incorporated herein by reference.

FIELD OF THE INVENTION

The present invention pertains to a gas-measuring arrangement with an open optical measuring section located in the free field.

BACKGROUND OF THE INVENTION

A gas sensor with a laser as the light source is known, for example, from U.S. Pat. No. 5,339,155 A, in which a gas-measuring arrangement with an open measuring section ("open-path sensor") is described, in which the laser light is directed via a semitransparent mirror and an obliquely positioned mirror onto a concave mirror and from there as a parallel light beam onto a reflector located at a remote location. The laser light is reflected by the reflector and the measuring section is passed through again, after which the reflected laser light falls again on the concave mirror, which focuses the reflected light onto the obliquely positioned mirror. The reflected laser light now travels from the obliquely positioned mirror to the laser light coupled in originally.

Part of the reflected laser light is then cast by the semitransparent mirror onto a detector, while another part is lost.

This arrangement of concave mirror, obliquely positioned decoupling mirror in the focal point of the concave mirror and detector corresponds, in principle, to the design of a Newton telescope, and a semitransparent mirror is additionally provided in the ray path for coupling in laser light and for decoupling reflected light onto the detector.

The analysis of gaseous mixtures has acquired increasing significance in both environmental analysis and process control and monitoring technology. The requirements imposed on the measuring systems in terms of measuring sensitivity, selectivity, long-term stability, maintenance intervals and service life increase with increasing degree of automation in industry and environmental monitoring.

To make it possible to recognize a gas being released, for example, in environmental analysis and monitoring technique as fast as possible, it is desirable to cover the areas to be monitored at the closest intervals possible and over as large an area as possible. A large number of sensors, which measure locally in narrowly limited areas, and which may be connected to one another via data connections, may be used for this. Far more advantageous and effective are, however, optically imaging gas sensors, in which the light emitted is directed over large measuring sections and wherein the absorption of the reflected light represents the gas species-specific measuring effect. Such systems make it possible to obtain data on the average gas concentration in the measuring section.

The length of the measuring section is limited by the losses of light over the measuring section itself, on the one hand, and other essential restrictions arise from the losses that occur due to the optical components, for example, the concave mirror, reflector and lens systems. To reduce the losses due to scattering, the light beam emitted must reach the reflector as a light beam extending in parallel over the entire length of the measuring section. Lasers as well as laser diodes are highly suitable light sources for such measuring systems, because they have a number of advantages over thermal light sources, and these advantages make them recommendable for gas measurement: high spectral intensity, high beam quality, narrow-band spectral emission, good modulation properties, and good opto-electric efficiency. As was mentioned above, gas sensor systems with open measuring section with imaging mirror array based on a Newton telescope design are known. The drawback of the prior-art systems is that optical elements attenuating the radiation, such as mirrors and beam splitters, are located in the main ray path and thus inevitably lead to a loss of light intensity.

If a polarization beam splitter is used for beam splitting, it is necessary for the polarization of the emitted light not to be changed through the measuring section itself and the reflecting mirror, because the prerequisite for low-loss decoupling of the reflected light onto the detector is otherwise not met.

Since neither the measuring section nor the reflecting mirror leave polarization unaffected, this has the consequence that a loss of light intensity develops in the polarization beam splitter, which reduces the light intensity of the reflected decoupled light. This in turn affects the measurement of the gas concentration, which can be analyzed by the detector, in terms of resolution, because the output signal of the detector is determined, on the one hand, by the light intensity of the incident light. The overall measuring resolution of the measuring system, which can be reached on the basis of the output signal, is additionally also determined by the signal-to-noise ratio of the detector. The same applies to lens systems for beam decoupling, so that there is basically an attenuation or reduction of the quantity of light sent to the detector for the measurement and hence of the available output signal.

SUMMARY OF THE INVENTION

An object of the present invention is to provide a gas-measuring arrangement for an open measuring section with low loss of intensity during the decoupling of the reflected light.

The arrangement according to the present invention comprises a light source, a first lens, a second lens, an obliquely positioned mirror with a central circular hole, a third lens, a phase mask and a reflecting mirror, as well as a fourth lens and a detector. The open measuring section is arranged between the phase mask and the reflecting mirror. The reflecting mirror at the end of the measuring section is illuminated essentially over its full area by a light beam. The laser beam bundle passes through an arrangement comprising a first lens and a second lens and subsequently passes through a round opening provided centrally in the mirror, is shaped by the third lens into a weakly divergent, essentially parallel light beam and directed through the phase mask towards the reflecting mirror arranged at a distant location as a slightly divergent light beam.

The mirror with its center and the opening is located in the focal point of the second lens for the emitted light beam, and the center of the mirror is in the focal point of the third lens for the reflected light beam. The reflecting mirror reflects back the light beam as a convergent light beam, the phase mask brings about in the focal point of the third lens a divergence of the reflected punctiform light beam, the so-called spot, into a circular ring, the so-called doughnut, in the center of which a dark zone of minimum light intensity is located. The phase mask works in the ideal case such that no light energy is present in the center of the ring and the extension of the zone of minimum light intensity in the focal point of the third lens is large compared to the round opening of the obliquely positioned mirror. Phase masks and spiral phase masks of such a type are known, for example, from "Mode-matched phase diffractive optical element for detecting laser modes with spiral phases," M. Golub, L. Shimski, N. Davidson, A. Friesem, Applied Optics, Vol. 46, No. 32, 2007, pp. 7823-7828. If the circular light ring with its internal diameter is larger than the opening in the mirror, which is made, for example, with a diameter of 5-10 µm, the light ring is decoupled from the reflected light beam by the mirror.

Thus, the reflected light cannot return through the obliquely positioned mirror to the light source, and the reflected light is therefore decoupled from the measuring section by the obliquely positioned mirror completely and nearly without loss and is sent via the fourth lens to the detector. An analysis unit determines a corresponding quantity of gas of the open measuring section from the signals of the detector.

This arrangement offers a number of advantages:

First, since no reflected light can return to the light source, the operation and control of the laser cannot be affected or interfered with. Second, the use of a beam splitter with light loss, e.g., in the form of an optical diode or a polarization beam splitter in the ray path, is not necessary for splitting emitted and reflected light. As a result, there also is no reduction in light intensity through the beam splitting elements. The light source of the measuring arrangement is preferably designed in the form of a solid laser, semiconductor laser, laser diode or gas discharge lamp.

The obliquely positioned mirror is preferably arranged at an angle of 45° in relation to the optical emission direction. However, an angle range from 10° to 60° in relation to the emission direction is also possible in an alternative variant. In an alternative embodiment, the reflecting mirror is not arranged at a wall located at a remote location, but at a housing part connected to the measuring device, and the optical measuring section is protected by means of a cover arranged at the housing part against effects of rain or snow on the measured signal.

In a preferred embodiment, the phase mask may be designed as a common component with the third lens.

The phase mask is designed as a spiral phase mask in a special embodiment variant.

Formula 1 describes the formation of the doughnut by a phase change P of the light through the spiral phase mask in the special embodiment variant in a complex notation in the exponential form.

$$P(r, \phi) = r \cdot e^{j \cdot n \cdot \phi}, \text{ in which } n: 1, 2,$$ Formula 1.

Variable n is an element from the range of natural numbers and describes the pitch of the spiral per $2\pi$ revolution of the circle.

The variables r and $\phi$ are polar coordinates, and j is the imaginary unit of the complex numbers.

In an alternative embodiment, the reflecting mirror may be designed as an arrangement comprising a plurality of retroreflectors.

In another preferred embodiment, the mirror may be designed as a coated glass plate or silicon plate, in which an uncoated zone is kept free in the center as a passage opening in the range of 5-10 µm for the passage of the emitted light beam. The coating may be prepared according to coating methods used in microsystems engineering, for example, physical gas phase deposition (PVD, sputtering) or by chemical gas phase deposition (CVD) combined with subsequent electroplating. The uncoated zones may be structured by photosensitive resist masking by means of photolithographic methods.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
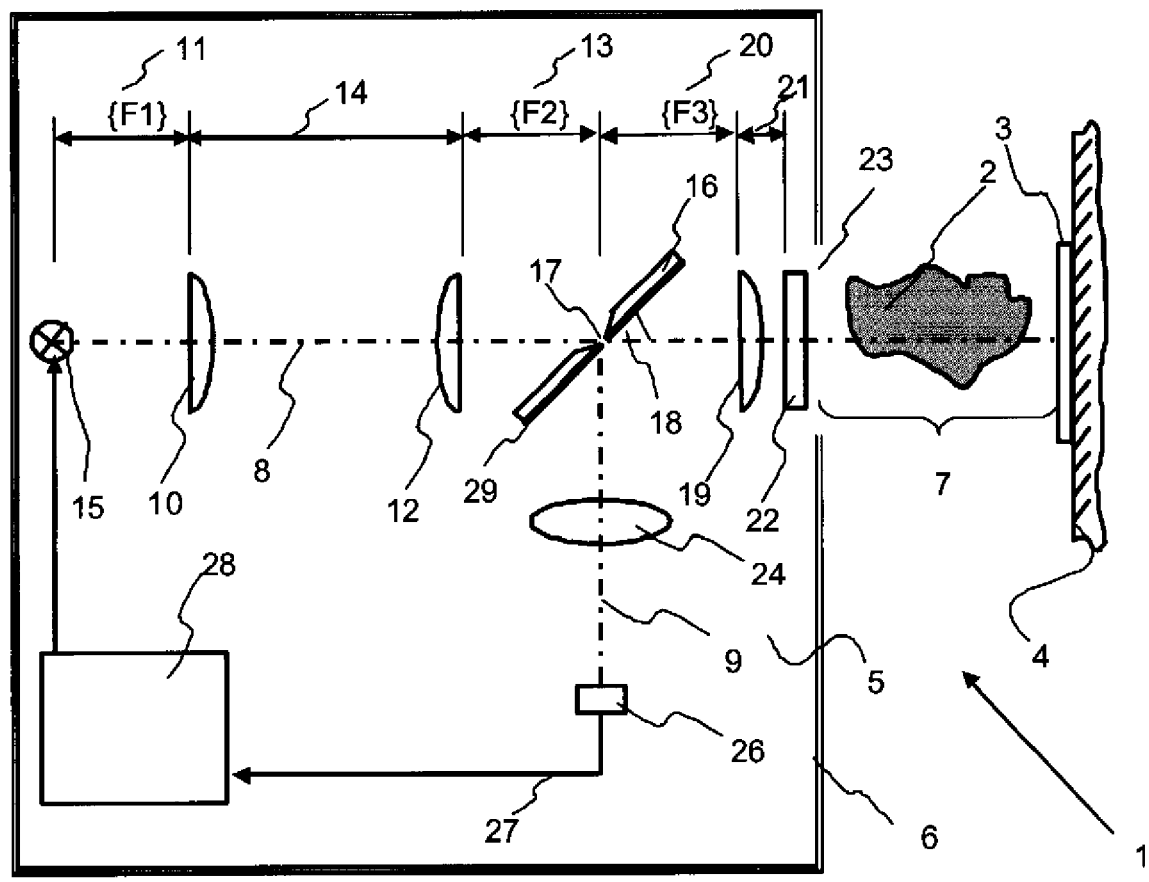
FIG. 1 is a view of the arrangement according to the present invention for measuring a gas with a phase mask and with an open measuring section.

Referring to the drawings in particular, FIG. 1 shows a measuring arrangement 1 according to the present invention for gas measurement with an open measuring section 7. The measuring arrangement 1 according to the present invention comprises a measuring device 5, the open measuring section 7 and a reflecting mirror 3 arranged at a wall 4 outside the measuring device 5. A quantity of gas 2, which can be detected by the measuring arrangement 1 according to the present invention, is present in the open measuring section 7. The measuring device 5 comprises a housing 6 with a light exit opening 23, the components for light emission: a light source 15, an array of a first, second and third lens 10, 12, 19, an obliquely positioned mirror (optical path mirror) 16 with a central opening 17 and with a mirror surface 29 pointing towards the open measuring section 7, as well as a phase mask 22, which is aligned with a first optical axis 8.

Other components of the measuring device 5 for detecting the reflected decoupled light are a fourth lens 24 and a detector 26, which are aligned with a second optical axis 9, as well as an analysis unit 28, which is connected to the detector 26 via a data and supply line 27.

Figure 1A:
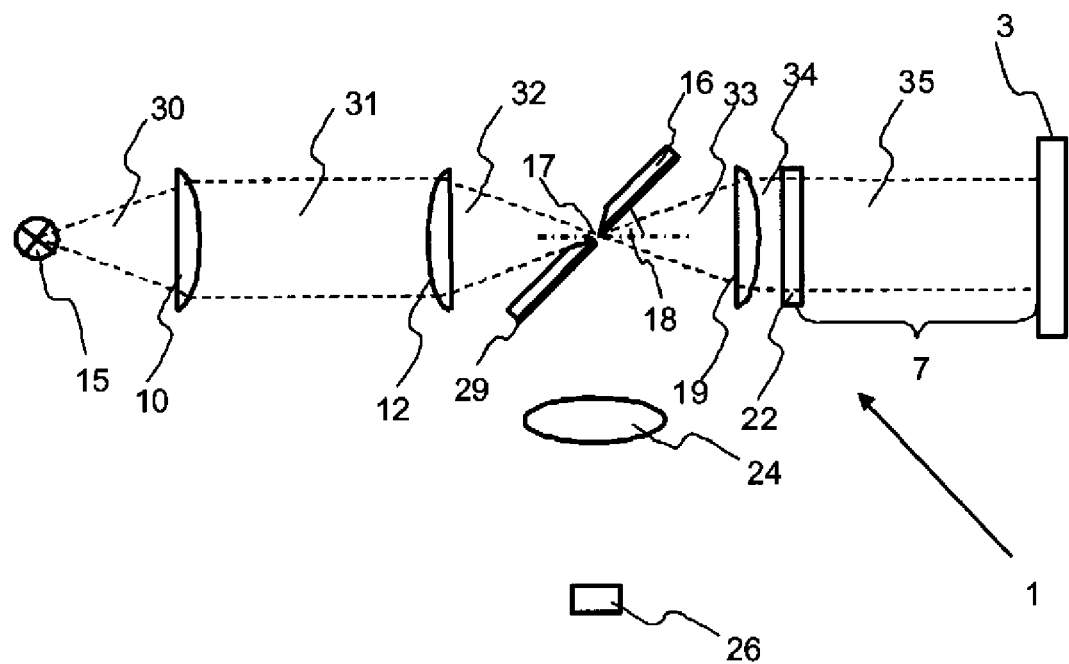
FIG. 1a is the path of the emitted light of the arrangement according to the present invention according to FIG. 1.

The path of the light emitted by the light source 15 through the measuring arrangement 1 according to FIG. 1 is shown on the basis of FIG. 1a and will be described in more detail below. The numbering of the distances of the lenses and focal distances thereof correspond to the numbering in FIG. 1.

A light source 15 is arranged in the focal point of a planoconvex first lens 10 of a first focal length {F1} 11, the light source 15 generates a first light beam 30, which is collimated via the first lens 10 into a parallel, second light beam 31.

A planoconvex second lens 12 with a second focal length {F2} 13 is arranged at a first distance 14. A mirror 16 positioned obliquely at an angle 18 of 45° in relation to the emission direction with a mirror surface 29 and an opening 17 is arranged in the focal point of the second lens 12.

The second lens 12 focuses the second light beam 31 into a third light beam 32, which exits from mirror 16 through the opening 17 of mirror 16 as a fourth light beam 33 in the focal point of the second lens 12 at the distance of the second focal length {F2} 13. The size of the third light beam can be varied at the site of opening 17 of mirror 16 by dimensioning the second focal length {F2} 13 of the second lens 12.

A planoconvex third lens 19 is arranged at the distance of a third focal length {F3} 20 of the third lens 19 from mirror 16.

The fourth light beam 33 is again collimated by the third lens 19 with the third focal length {F3} 20 into a fifth light beam 34, and this passes through a phase mask 22 arranged at the second distance 21, its phase is changed by this phase mask 22 for the first time, and is sent as a sixth light beam 35 via the open measuring section 7 to a reflecting mirror 3.

Figure 1B:
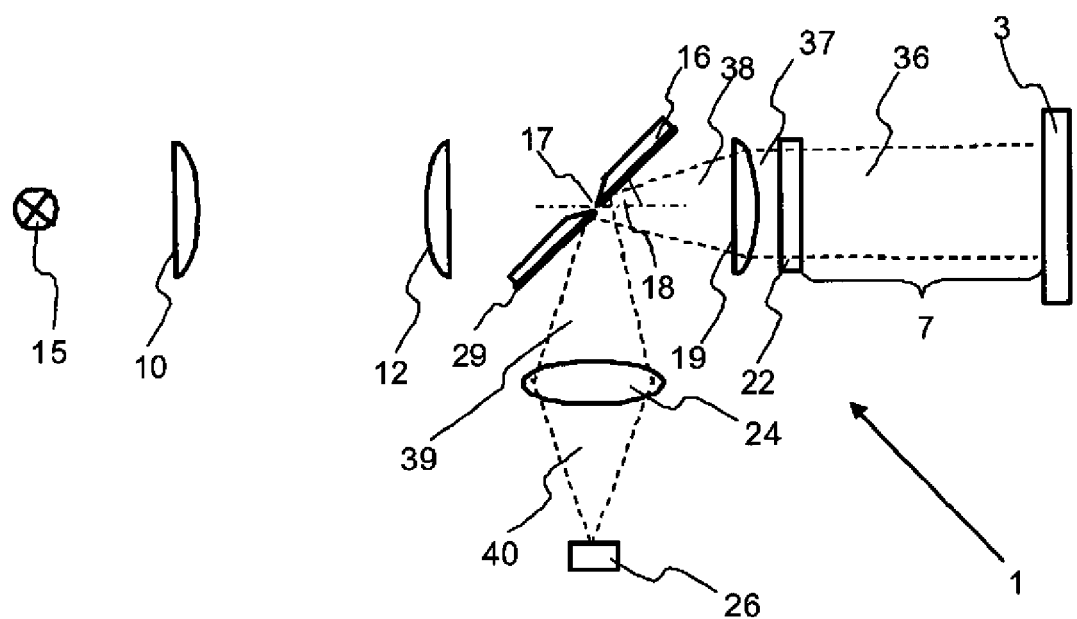
FIG. 1b is the path of the reflected light of the arrangement according to the present invention according to FIG. 1.

The path of the reflected light from the reflecting mirror 3 to the detector 26 is shown on the basis of FIG. 1b and will be described in more detail below. The numbering of the distances of the lenses and the focal lengths thereof correspond to the numbering in FIG. 1.

Figure 2:
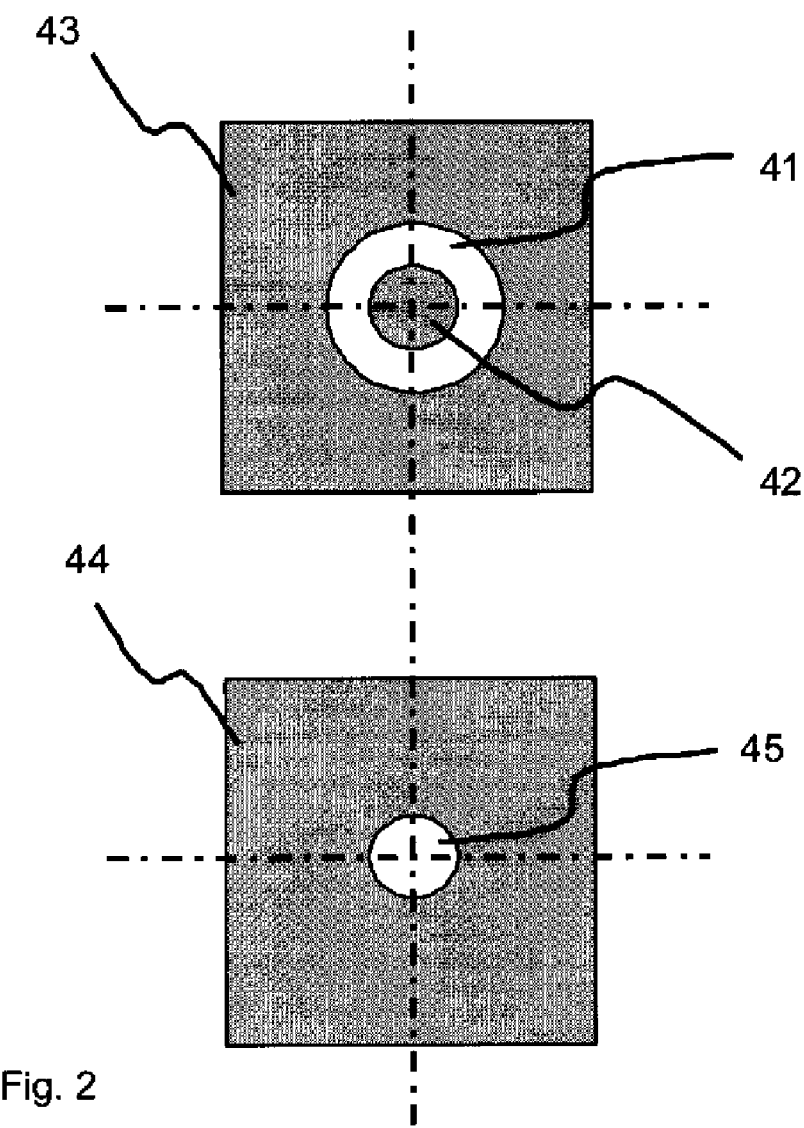
FIG. 2 is a view of the reflected light bundle at the site of the mirror.

The reflecting mirror 3 reflects back the light as a seventh light beam 36. The phase of the seventh light beam 36 is changed by the phase mask 22 for the second time and is sent as an eighth light beam 37 to the third lens 19. The change in shape, which the seventh light beam 36 undergoes due to the phase mask 22 in the focal point of the third lens 19, is shown by the first two-dimensional view 43 of the eighth light beam 37, which is shown in FIG. 2, in the form of a light intensity ring 41 with a central dark spot 42. The second two-dimensional image 44 of a light intensity spot 45, which is likewise shown in FIG. 2, corresponds to the unchanged phase position of the seventh light beam 36 in the focal point of the third lens 19, i.e., to a measuring arrangement 1 without a phase mask 22.

The light reaches mirror 16 as a ninth light beam 38 through the phase mask 22 and the third lens 19. Mirror 16 is arranged with its center in the focal point of the third focal length {F3} 20 of the third lens 19. Since the dimension of light intensity ring 41 is larger than opening 17 of mirror 16, it is decoupled on the side as a tenth light beam 39 through the mirror surface 29 of mirror 16 and thus it does not return to the light source 15 through opening 17 of mirror 16.

A biconvex fourth lens 24 focuses the tenth light beam 39 as an eleventh light beam 40 on detector 26. Detector 26 detects the intensity of the eleventh light beam 40 and sends the detected signal via the data and supply line 27 to the analysis unit 28. The quantity of gas 2 present along the open measuring section 7 affects the spectral intensities of the detected light and hence the output signal of detector 26 as a function of the gases contained in the quantity of gas 2. Analysis unit 28 determines from this the corresponding quantity of gas 2.

FIG. 2 shows the change in shape of a light beam through the phase mask 22 as a first two-dimensional view 43 in the form of a light intensity ring 41 with a central dark spot 42. The first (upper view) two-dimensional view 43 corresponds to a view as it can also be found in Mode-matched phase diffractive optical element for detecting laser modes with spiral phases. M. Golub, L. Shimski, N. Davidson, A. Friesem, Applied Optics, Vol. 46, No. 32, 2007, p. 7826. The second (lower view) two-dimensional image 44 in FIG. 2 shows a light intensity spot 45 without being affected by a phase mask 22.

Figure 3:
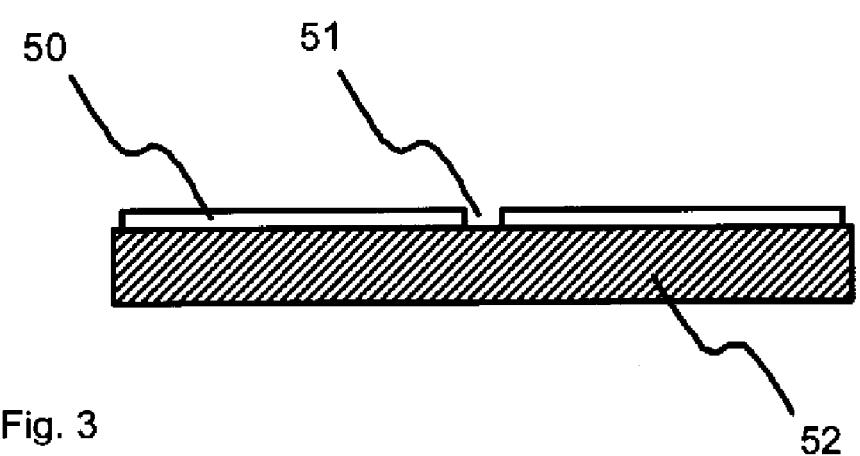
FIG. 3 is a view of an embodiment of the obliquely positioned mirror in the form of a coated glass plate.

FIG. 3 shows a glass plate 52, whose surface is provided with a coating 50, which is structured such that an uncoated zone 51 is formed, which acts as an opening 17 for the passage of light through mirror 16.

Figure 4:
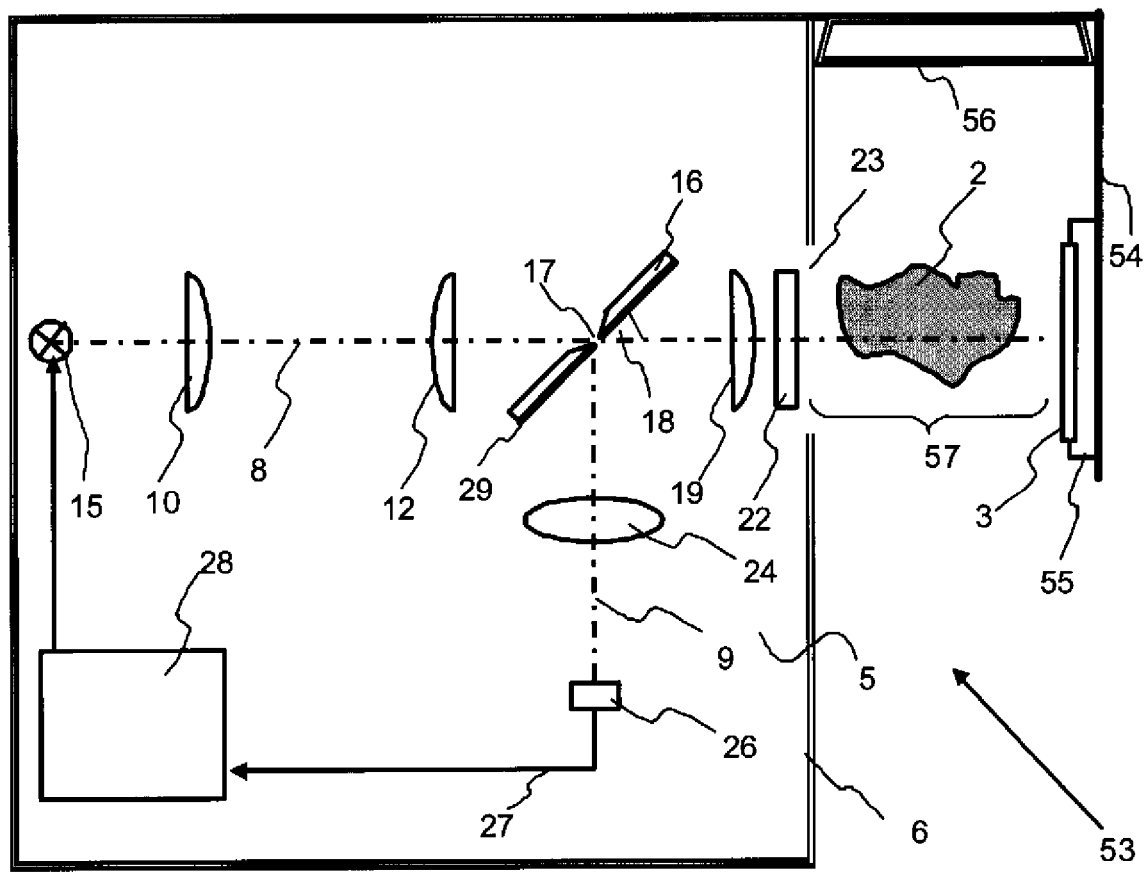
FIG. 4 is an alternative measuring arrangement according to FIG. 1.

FIG. 4 shows an alternative measuring arrangement 53 according to FIG. 1. Identical components are designated by the same reference numbers. The reflecting mirror 3 is arranged by means of a bracket 55 at a housing part 54 connected to the measuring device 5, and an inner measuring section 57 is arranged directly at the measuring device 5 and is protected from weather effects by means of a cover 56 on the top side. Cover 56 is connected to the housing part 54 and to the measuring device 5 proper.

While specific embodiments of the invention have been shown and described in detail to illustrate the application of the principles of the invention, it will be understood that the invention may be embodied otherwise without departing from such principles.

LIST OF REFERENCE NUMBERS

1 Measuring arrangement
2 Quantity of gas
3 Reflecting mirror
4 Wall
5 Measuring device
6 Housing
7 Open measuring section
8 First optical axis
9 Second optical axis
10 First lens
11 First focal length {F1}
12 Second lens
13 Second focal length {F2}
14 First distance
15 Light source
16 Mirror
17 Opening
18 Angle
19 Third lens
20 Third focal length {F3}
21 Second distance
22 Phase mask
23 Light exit opening
24 Fourth lens
26 Detector
27 Data and supply line
28 Analysis unit
29 Mirror surface
30 First light beam
31 Second light beam
32 Third light beam
33 Fourth light beam
34 Fifth light beam
35 Sixth light beam
36 Seventh light beam
37 Eighth light beam
38 Ninth light beam
39 Tenth light beam
40 Eleventh light beam
41 Light intensity ring
42 Central dark spot
43 First two-dimensional view
44 Second two-dimensional view
45 Light intensity spot
50 Coating
52 Glass plate
53 Alternative measuring arrangement
54 Housing part
55 Bracket
56 Cover
57 Inner measuring section

What is claimed is:

1. A measuring arrangement comprising:
a measuring device with an open section, the measuring device for determining an average quantity of gas along said open measuring section, the measuring device including a light source, an optical path mirror, a reflecting mirror and a detector with a phase mask; wherein:
the light of the light source passes through the open measuring section through an opening in said optical path mirror along a first optical axis and falls on said reflecting mirror;
the light is reflected back to said optical path mirror by said reflecting mirror and the light is decoupled to said detector with said phase mask located between the reflecting mirror and said optical path mirror; and
said phase mask brings about a decoupling of the light by diverging light reflected by said reflecting mirror.

2. A measuring arrangement in accordance with claim 1, wherein the decoupling of the light through said phase mask is brought about by the phase of the light reflected by said reflecting mirror being changed in such a way that a light intensity spot is diverged into a light intensity ring.

3. A measuring arrangement in accordance with claim 2, wherein the light intensity ring has a larger dimension compared to a dimension of said opening of said optical path mirror and wherein the light reflected by said reflecting mirror cannot return back to the light source through said opening of said optical path mirror.

4. A measuring arrangement in accordance with claim 3, wherein:
said light intensity ring is deflected by said optical path mirror along a second optical axis to said detector; and
said measuring device further comprises an analysis unit for determining a corresponding quantity of gas from signals of said detector.

5. A measuring arrangement in accordance with claim 1, wherein said optical path mirror is arranged with an angle, in an angle range of 10° to 60°, in relation to said optical axis.

6. A measuring arrangement in accordance with claim 1, wherein said optical path mirror is arranged at an angle of 45° in relation to said optical axis.

7. A measuring arrangement in accordance with claim 1, wherein the reflecting mirror comprises an array of a plurality of retroreflectors.

8. A measuring arrangement in accordance with claim 1, wherein said optical path mirror comprises a glass plate and a mirror surface applied to said glass plate as a structured coating.

9. A measuring arrangement in accordance with claim 1, wherein said phase mask is provided with a lens as a common component.

10. A measuring arrangement in accordance with claim 1, wherein said phase mask comprises a spiral phase mask.

11. A measuring arrangement in accordance with claim 1, wherein said light source comprises a solid laser.

12. A measuring arrangement in accordance with claim 1, wherein said light source comprises a laser diode.

13. A measuring arrangement in accordance with claim 1, wherein said light source comprises a semiconductor laser.

14. A measuring arrangement in accordance with claim 1, wherein said light source comprises a gas discharge lamp.

15. A measuring arrangement in accordance with claim 1, wherein said open measuring section is located outside said measuring device.

16. A measuring arrangement in accordance with claim 1, wherein said reflecting mirror is arranged at a housing part connected to said measuring device and wherein a cover protects an inner measuring section against weather effects.

17. A measuring arrangement comprising:
a measuring device housing with an opening leading to an open section;
a light source disposed in said measuring device housing and generating light with an initial light path along a measuring device optical axis;
an optical path mirror disposed in said measuring device housing, said optical path mirror having an opening through which said optical axis extends;
a reflecting mirror disposed adjacent to said open section;
a detector disposed in said measuring device housing;
a phase mask disposed in said measuring device housing, wherein said light of the light source passes through said opening in said optical path mirror along said first optical axis and passes through said open measuring section to said reflecting mirror, reflected light is reflected to said optical path mirror by said reflecting mirror and light is decoupled to said detector with said phase mask located between said reflecting mirror and said optical path mirror and said phase mask brings about a decoupling of the light by diverging light reflected by said reflecting mirror, said light source, said optical path mirror, said reflecting mirror, said detector and said phase mask forming a measuring device for determining an average quantity of gas along said open measuring section.

18. A measuring arrangement in accordance with claim 17, wherein the decoupling of the light through said phase mask is brought about by the phase of the light reflected by said reflecting mirror being changed in such a way that a light intensity spot is diverged into a light intensity ring, wherein the light intensity ring has a larger dimension compared to a dimension of said opening of said optical path mirror and wherein the light reflected by said reflecting mirror cannot return back to the light source through said opening of said optical path mirror.

19. A measuring arrangement in accordance with claim 18, wherein:
said light intensity ring is deflected by said optical path mirror along another optical axis to said detector; and
said measuring device further comprises an analysis unit for determining a corresponding quantity of gas from signals of said detector.

20. A measuring arrangement in accordance with claim 17, wherein said open measuring section is located outside said measuring device housing and said reflecting mirror is arranged at a housing part connected to said measuring device housing and wherein a cover protects an inner measuring section against weather effects.

* * * * *